United States Patent [19]
Azuma et al.

[11] Patent Number: 5,211,943
[45] Date of Patent: May 18, 1993

[54] PHARMACEUTICAL PREPARATION FOR ADMINISTRATION BY PERCUTANEOUS ABSORPTION AND A METHOD FOR THEIR MANUFACTURE

[75] Inventors: Masato Azuma, Osaka; Toshihiro Inoue, Hyogo; Yasuaki Kawano, Saitama, all of Japan

[73] Assignees: Chugai Seiyaku Kabushili Kaisha, Tokyo; Sekisui Kagaku Kogyo Kabushiki Kaisha, Osaka, both of Japan

[21] Appl. No.: 86,319

[22] Filed: Aug. 14, 1987

[30] Foreign Application Priority Data

Aug. 18, 1986 [JP] Japan .................. 61-192492
Aug. 18, 1986 [JP] Japan .................. 61-192493
Apr. 1, 1987 [JP] Japan .................. 62-80276

[51] Int. Cl.$^5$ .................. A61K 31/745; A01J 21/00
[52] U.S. Cl. .................. 424/448; 424/484; 424/449; 424/489; 514/355
[58] Field of Search .................. 424/447, 83, 78

[56] References Cited

U.S. PATENT DOCUMENTS 4,200,640 4/1980 Nagano et al. .................. 424/266
4,690,683 9/1987 Chien et al. .................. 424/449

FOREIGN PATENT DOCUMENTS 156080 10/1985 European Pat. Off. .
0185347 6/1986 European Pat. Off. .
3536669 4/1986 Fed. Rep. of Germany .
59-10513 11/1984 Japan .
60-184010 9/1985 Japan .................. 424/449

OTHER PUBLICATIONS

Chemical Abstracts, vol. 105, No. 6, 11th Aug. 1986, p. 397, abstract No. 49085g, Columbus, Ohio, US; & JA-A-61 78 720 (Rhone-Poulenc Sante)/Apr. 22, 1986.
Patent Abstracts of Japan, vol. 8, No. 93 (C-220) (1530), 27th Apr. 1984; & JP-A-59 10 513 (Nitto Denki Kogyo K.K.) Jan. 20, 1984.

Primary Examiner—Thurman K. Page
Assistant Examiner—Peter F. Kulkosky
Attorney, Agent, or Firm—Browdy and Neimark

[57] ABSTRACT

A pharmaceutical preparation for percutaneous absorption comprising a base material and fine crystals of Nicorandil and/or salts of Nicorandil that are evenly distributed throughout said base material and that have a mean diameter of 2 μm or more, and a method for preparing the same.

42 Claims, No Drawings

PHARMACEUTICAL PREPARATION FOR ADMINISTRATION BY PERCUTANEOUS ABSORPTION AND A METHOD FOR THEIR MANUFACTURE

BACKGROUND OF THE INVENTION

1. Field of the Invention

This invention relates to pharmaceutical preparations for administration by percutaneous absorption that contain Nicorandil and to a method for their manufacture. More particularly, it relates to pharmaceutical preparations for administration by percutaneous absorption such as tapes and/or sheets (hereinafter refer to as tapes) and ointments, etc., that have excellent absorbability through the skin and that moreover are very stable in terms of the ingredients of the pharmaceutical agents contained therein.

2. Description of the Prior Art

Nicorandil, or N-(2-hydroxyethyl)nicotinamide nitrate, is an effective drug for the treatment of angina pectoris caused by many kinds of disorders, as it acts to dilate the coronary vessels and to inhibit contractions of the coronary veins, without much effect on the blood flow through the heart or on heart function (Japanese Patent Publication 58-17463). This Nicorandil is commercially available as a drug to be taken orally. However, in general, when a drug is taken orally, its rate of absorption varies according to the conditions in the stomach and the intestines, such as the pH, the present or absence of other contents, etc., and so it is difficult for the drug to be absorbed gradually at a steady rate over a long period of time. When the Nicorandil mentioned above is given orally, it sometimes causes side effects such as orthostatic hypotension and headache, caused when there is a rapid increase of the level of this agent in the blood.

It is known that some drugs for which it is difficult to achieve a uniform rate of absorption by the oral route can be given in the form of a pharmaceutical preparation with administration by percutaneous absorption. One typical drug for angina pectoris is a preparation of nitroglycerin in tape form (Japanese Patent Laid-Open 56-133381). A preparation of the Nicorandil mentioned above in tape form has also been proposed. For example, in Japanese Patent Laid-Open 59-10513, it has been proposed that a polymer with a glass transition point, $T_g$, of $-70°$ to $-10°$ C. and with the property of adhesion with pressure at ordinary temperatures be bound to Nicorandil, and that this pharmaceutical preparation be made into tape form by being layered onto a support.

In the pharmaceutical preparation in tape form disclosed in Japanese Patent Laid-Open 59-10513 mentioned above, the basic necessary conditions are given, such as that the structure of the polymer that makes up the base material must be suitably compatible with the Nicorandil, that the greater part of the Nicorandil must not become crystallized in the base material, that the Nicorandil is supplied from the base material at a rate suitable for absorption into the skin, etc. However, Nicorandil is relatively unstable at conditions of high temperature or high humidity, or in solution (Iyakuhin Kenkyu, vol. 14 (issue 6), pp. 968–979, 1983), and among the agents absorbed percutaneously that satisfy the conditions mentioned above in the report, Nicorandil is extremely unstable, and the stability during storage for long periods of time needed for pharmaceutical preparations cannot be ensured.

SUMMARY OF THE INVENTION

The pharmaceutical preparation with administration by percutaneous absorption of this invention, which overcomes the above-discussed and numerous other disadvantages and deficiencies of the prior art, comprises a base material and fine crystals of Nicorandil and/or the Nicorandil salt that are evenly distributed throughout said base material and that have a mean diameter of 2 μm or more.

In a preferred embodiment, the pharmaceutical preparation mentioned above has absorbefacients for percutaneous absorption.

In a preferred embodiment, the mean diameter of granules of the Nicorandil and/or its salt mentioned above is 4–30 μm.

In a preferred embodiment, the pharmaceutical preparation mentioned above is a tape or an ointment.

The method for the manufacture of the pharmaceutical preparation for administration by percutaneous absorption of this invention comprises dissolving the Nicorandil and/or its salt in a solvent that is a good solvent for said Nicorandil, and dissolving the base material in a solvent that is a poor solvent for said Nicorandil, mixing these two solutions to give a solution of a mixture that contains precipitated crystals of Nicorandil with a mean diameter of 2–30 μm, and substantially removing said good solvent and said poor solvent from said solution of the mixture.

In a preferred embodiment, the solution of the mixture mentioned above has absorbefacient for percutaneous absorption.

In a preferred embodiment, the method mentioned above involves the application of the solution mixture mentioned above to a support, and the substantial removal of the solvents by drying, resulting in a tape with an adhesive layer that contains said Nicorandil on the flexible support.

In a preferred embodiment, the base material mentioned above is hydrophobic.

In a preferred embodiment, the base material mentioned above is an adhesive rubber base material.

In a preferred embodiment, the adhesive rubber base material mentioned above is 1,4-cis-polybutadiene.

In a preferred embodiment, the adhesive rubber base material is an adhesive of silicone rubber.

In a preferred embodiment, the salt of Nicorandil mentioned above is a salt of Nicorandil and an organic acid, and the organic acid is at least one selected from the group consisting of fumaric acid, oxalic acid, salicylic acid, tartaric acid, glutaric acid, maleic acid and p-toluenesulfonic acid.

In a preferred embodiment, the absorbefacient for percutaneous absorption mentioned above is 1-dodecylazacycloheptane-2-one.

In a preferred embodiment, the absorbefacient for percutaneous absorption mentioned above is a combination of the fatty acid esters and compounds that have an amide bond, and the compounds that have an amide bond include at least one selected from the group consisting of N-acylsarcosine, monoethanolamides derived from fatty acids, diethanolamides derived from fatty acids, alkyleneoxide adducts of monoethanolamides derived from fatty acids, and alkyleneoxide adducts of diethanolamides derived from fatty acids.

In a preferred embodiment, the good solvent mentioned above is at least one selected from the group consisting of tetrahydrofuran, dichloromethane, and chloroform and the poor solvent mentioned above is at least one selected from the group consisting of n-hexane, cyclohexane, n-pentane, cyclopentane, n-heptane, cycloheptane, toluene, and freon.

Thus, the invention disclosed herein makes possible the objects of (1) providing a pharmaceutical preparation for administration by percutaneous absorption in which the stability of the Nicorandil and/or Nicorandil salt used therein as a drug is excellent, so that it is possible to store the preparation for long periods of time, and in which, moreover, the release and/or absorbability of said drug via the skin at the time of use are excellent; (2) providing a tape or an ointment that has the excellent properties described above in (1); and (3) providing a method for the ready manufacture of the preparation that has the excellent properties mentioned above in (1).

DESCRIPTION OF THE PREFERRED EMBODIMENTS

As the base material to be used in the pharmaceutical preparation of this invention, any of those base materials that are commonly used in tapes and ointments can be used, with the kind selected in accordance with the purposes of this pharmaceutical preparation. In general, hydrophobic base materials are selected in consideration of the adhesion to the skin, the rate of supply of the drug from the pharmaceutical preparation, and the stability of the drugs contained therein.

As the base material for an ointment, plastibase, white vaseline, liquid paraffin, or fatty triglycerides with three alkyl chains of medium length, and preferably plastibase, white vaseline, and liquid paraffin, are used.

As the base material for a tape, in general, base materials that have pressure-adhesive properties at ordinary temperatures can be used. These include polyvinylalkylether, poly(metha)acrylate, polyurethane, polyamide, ethylene-vinylacetate copolymer, alkylacrylate-acrylic acid copolymer, polyisoprene rubber, SIS (styrene-isoprene-styrene block copolymer), styrene-butadiene rubber, polyisobutylene rubber, isobutylene-isoprene rubber, natural rubber, 1,4-cis-polybutadiene and silicone rubber. Polyisoprene rubber, polyisobutylene rubber, isobutylene-isoprene rubber, 1,4-cis-polybutadiene, silicone rubber, etc., which have almost no compatibility with Nicorandil, are particularly preferred. Moreover, of the base materials mentioned above, rubber-type base materials, and in particular, base materials that contain 1,4-cis-polybutadiene, or silicone rubber are preferable. The 1,4-cis-polybutadiene mentioned above is preferably used in a proportion of 20-80% by weight in the base material. The inclusion of 1(-4-cis-polybutadiene increases the stability and the release of the Nicorandil. If the proportion of 1,4-cis-polybutadiene is more than 80% by weight, the adhesion of the preparation is somewhat decreased.

The base materials listed above can be used in mixtures of two kinds or more, and stabilizers, preservatives, dispersing agents, tackifiers, softening agents, fillers, antioxidants, etc., can be added as needed.

The Nicorandil that is contained in the pharmaceutical preparation can also be in the form of the Nicorandil salt. As the Nicorandil salt, there are organic acids and/or inorganic acids of Nicorandil that are pharmaceutically acceptable. As acids from which Nicorandil salt can be formed, there are hydrochloric acid, oxalic acid, p-toluenesulfonic acid, fumaric acid, maleic acid, salicylic acid, tartaric acid, glutaric acid, etc. By the formation of the salt of Nicorandil, the stability is increased. For the Nicorandil salt, either a salt made beforehand by the addition of an acid from the list given above to Nicorandil can be used, or a salt made during the preparation of the pharmaceutical (described below) can be used, at which time the salt is formed by the addition of an acid from the list given above to the mixture of base material, etc. When acid is added in the latter case, said acid can be added in a proportion of 0.1% by weight or more of the entire mixture, and preferably, 0.1-20% by weight can be added. In these calculations of proportions, the entire content of the pharmaceutical preparation is meant in the case of an ointment, and the content with the support excluded is meant in the case of a tape. The meaning of content as used below in the discussions of absorbefacient content, etc., is the same as here.

The proportions of the Nicorandil and/or its salt (herein referred to as the Nicorandil (salt)) can be 0.1-30% by weight in the pharmaceutical preparation, and preferably, 2-15% by weight. Because the base materials that can be used in this invention have poor compatibility with Nicorandil (salt), most of the Nicorandil (salt) that is contained in the pharmaceutical preparation at the proportions mentioned above is dispersed throughout the base. The granule size of said drug at this time can be 2 $\mu$m or more. If the mean diameter is less than 2 $\mu$m, the stability decreases. There is no particular upper limit for the diameter of the granules, but a diameter of 50 $\mu$m or less is desirable for satisfactory release of the drug. A diameter of said drug of from 4 to 30 $\mu$m is more preferable. This diameter of the granules as defined in this text is obtained by Feret diameters under a microscope (Powders Engineering by Shigeo Miwa; Asakura Books).

Methods that can b used to bring the Nicorandil (salt) mentioned above to the granule size mentioned above include a method of powdering said drug in a ball mill powdering it in a jet mill, etc., and then sieving it to obtain the preferred size; and a method in which Nicorandil (salt) is precipitated in the form of fine particles by the use of a poor solvent from a solution containing the Nicorandil (salt), etc.

The pharmaceutical preparation of this invention may contain absorbefacient for percutaneous absorption, so as to increase the absorbability of the drug mentioned above. There are no particular limits on which absorbefacients for percutaneous absorption can be used, but 1-dodecylazacycloheptane-2-one and/or a mixture of compounds that have an amide bond with fatty acid esters are particularly suitable. The compounds that have an amide bond, include at least one selected from the groups consisting of N-acylsarcosine, monoethanolamides derived from fatty acids, diethanolamides derived from fatty acids, alkyleneoxide adducts of monoethanolamides derived from fatty acids, and alkyleneoxide adducts of diethanolamides derived from fatty acids. Of course, absorbefacients other than those listed above can be used.

The absorbefacient mentioned above, 1-dodecylazacycloheptane-2-one, is available commercially from Nelson Research and Development Co., U.S.A., under the trade name of AZONE ®. This compound is known for being added as an absorbefacient for percutaneous absorption to drugs such as anti-inflammatory agents, antifungal agents, etc. (Japanese Patent Laid-Open 52-1035, ditto 57-142918 ditto 58-210026, ditto 58-208216, ditto 61-27966). In addition, this compound is known for being used as an absorbefacient for absorption through the mucosa of the said drugs (Japanese Patent Laid-Open 61-109738). However, it has not yet been known as an absorbefacient for the absorption of Nicorandil. This absorbefacient can be added to the pharmaceutical preparation in a proportion of 10% by weight or less of the total weight, and preferably in a proportion of 2–6% by weight.

The fatty acid esters of the absorbefacients mentioned above can be used in combination with a compound that has an amide bond. These esters of fatty acids are formed by the reaction of fatty acids with alcohol. It is preferable that the carbon number of the fatty acids be from 10 to 18, and that the number of carbons in the alcohol be from 1 to 20. As such fatty acids, there are capric acid, lauric acid, myristic acid, palmitic acid stearic acid, oleic acid, sebacic acid, adipic acid, etc.; as such alcohols, there are methanol, ethanol, propanol, isopropanol, glycerin, etc. As the fatty acid esters formed from the fatty acids and alcohols listed above, there are, for example, isopropyl caprate, propyl laurate, octyldodecyl myristate, myristyl myristate, isopropyl myristate, isopropyl palmitate, ethyl stearate, and methyl sebacate. Of these, isopropyl myristate and isopropyl palmitate are especially suitable. The fatty acid esters can be present in the proportion of 80% by weight or less, preferably 1–80 parts by weight, and more preferably 10–60 parts by weight to 100 parts by weight of the base material. That this fatty acid ester can be mixed with propylene glycol so as to be used as an absorbefacient for the absorption of Nicorandil is known (107th annual meeting of the Pharmaceutical Society of Japan, Proceedings, p. 841, Mar. 10, 1987).

Of the compounds that have an amide bond, N-acylsarcosine is sarcosine (N-methylglycine) with the acyl group having 6–18 carbons replaced with the nitrogen of amino groups. Its structure is as shown in the formula (I) below.

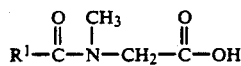

where $R^1$ is an aliphatic hydrocarbyl group with 5–17 carbons.

The above compound (I), N-acylsarcosine, is a sarcosine derivative of fatty acids with 6–18 carbons. As fatty acids for the formation of N-acylsarcosine, there include, among other compounds: caproic acid, enanthic acid caprylic acid, pelargonic aid, capric acid, lauric acid myristic acid, palmitic acid, margaric acid, stearic acid, hexadecenoic acid, oleic acid, and linoleic acid. The salt of N-acylsarcosine can also be used. Of the different forms of N-acylsarcosine, the lauric acid derivative, lauroylsarcosine, and its salt give particularly good results. The proportion of N-acylsarcosine that can be used is 30 parts by weight or less, and preferably, 0.01–30 parts by weight; more preferably, 0.5–10 parts by weight to 100 parts by weight of the base material should be used.

Of the compounds that have an amide bond mentioned above, the structures of monoethanolamides derived from fatty acids (II) and diethanolamides derived from fatty acids (III) are as shown in the formulae below.

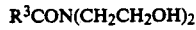

where $R^2$ and $R^3$ are aliphatic hydrocarbyl groups with 5–17 carbons.

Monoethanolamides derived from fatty acids (II) are formed by a reaction of fatty acids with monoethanolamine, and diethanolamides derived from fatty acids (III) are formed by the reaction of fatty acids with diethanolamine. The fatty acids from which compounds (II) and (III) can be formed have 6–18 carbons (corresponding to an $R^2$ or $R^3$ of 5–17). Of such fatty acids, octanoic acid, capric acid, lauric acid, myristic acid, etc., can be mentioned. It is also suitable to use fatty acids derived from coconut oil, which is a mixture of the compounds above. Of the compounds that have the structural formula of (II) or (III), lauroylmonoethanolamide and lauroyldiethanolamide are particularly preferred.

As the compound that has an amide bond, compounds with the structures of (II) or (III) above to which alkyleneoxide is added (that is, polyoxyalkylene monoethanolamides derived from fatty acids, and polyoxyalkylene diethanolamides derived from fatty acids) can also be used. The moles of alkyleneoxide that can be added are 1–40, and preferably 2–20. Here, by "one mole is added" we mean, for the case of monoethanolamides derived from fatty acids, that one molecule of alkyleneoxide is added to the hydroxyl group in said molecule, and, for the case of diethanolamides derived from fatty acids, that for each of the two hydroxyl groups in said molecules, one molecule of alkyleneoxide is added to each. For the alkyleneoxide, ethylene oxide is suitable.

The above-mentioned N-acylsarcosine, monoethanolamides derived from fatty acids, diethanolamides derived from fatty acids, alkyleneoxide adducts of monoethanolamides derived from fatty acids, and alkyleneoxide adducts of diethanolamides derived from fatty acids can be mixed together with two or more of the compounds in the mixture, and can be used in a mixture with the further addition of the fatty acid esters mentioned above. These compounds that have an amide bond can be contained in a proportion of 30 parts by weight or less, preferably 0.5–10 parts by weight, and more preferably 0.5–10 parts by weight to 100 parts by weight of the base material, with only one or with a mixture of the compounds having an amide bond being used.

By the inclusion of an absorbefacient as mentioned above, Nicorandil (salt) is absorbed more quickly through the skin. Of the total weight of the formulation, the absorbefacient can be contained in a proportion of 100 parts by weight or less, and preferably 1–100 parts by weight to 100 parts by weight of the base material. If there is an excess, for example, the compatibility with the base material may be worsened, and the adhesive properties of the pharmaceutical preparation in the form of a tape may be decreased.

The support to be used when the pharmaceutical preparation of this invention is in the form of a tape can be formed at the surface of the base layer; moreover, there are no particular limits on suitable substances that are flexible provided that the flexibility is sufficient to ensure that there is no feeling of physical discomfort on the skin surface when the tape is being used. For example, films sheets, non-woven cloth, cloth, etc., made from polyolefin, polyurethane, polyvinylalcohol, polyvinylidenechloride, polyamide, ethylene-vinylacetate copolymer, rubber, etc., can be used.

The pharmaceutical preparation of this invention can be obtained by, for example, the following method. First, powdered or solid Nicorandil (salt) is powdered in a ball mill, jet mill, etc., to give Nicorandil (salt) of the desired granule size prepared in advance. Next, the base material is dissolved in a solvent that is a poor solvent for the Nicorandil (salt) and a good solvent for the base material, and then the prepared Nicorandil (salt) of the desired granule size mentioned above is dispersed uniformly in the solution. The kind of base material is chosen so as to be appropriate for the intended use (whether a tape or an ointment). When a tape is to be obtained, this suspension can be painted onto the top of a support and dried so as to form an adhesive layer. It is also possible to obtain a tape by applying the above-mentioned suspension onto a suitable separating paper, and after drying it there, pasting the adhesive layer formed onto the top of the support mentioned above. An ointment can be obtained by a mixing method in which the granules or desired size of Nicorandil (salt) mentioned above are mixed directly with the base material together with other ingredients such as an absorbefacient if needed, or by other methods such as a method in which almost all of the solvent from the suspension is removed as mentioned above, etc.

A pharmaceutical preparation that contains crystals of Nicorandil (salt) dispersed in a base material can be obtained, for example, as a tape by the application of a solution in which the Nicorandil (salt), base material, etc., are completely dissolved onto a support, and then by the removal of the solvent. However, in this method, there are several defects, such as that Nicorandil (salt) can be widely deposited from adhesive matrix onto the surface of adhesive layer, resulting in a lowered adhesion of the adhesive layer, that the absorption of the Nicorandil (salt) can decrease because large crystals of Nicorandil (salt) will gradually precipitate out, etc.

In all of the methods mentioned above that use a fine powder of Nicorandil (salt), depending on the conditions of its manufacture, the powder particles of Nicorandil (salt) can adhere to each other during storage, and the particles can also adhere to each other in the dispersed solution, both of which are inconvenient. To avoid this, the following method of preparation can be recommended. First of all, for example, Nicorandil (salt) is dissolved in an appropriate good solvent. As the good solvent, tetrahydrofuran, dichloromethane, chloroform, etc., can be used. The concentration of Nicorandil (salt) is about 1-40% by weight. Next, the base material mentioned above is dissolved in a solvent that is a poor solvent for Nicorandil (salt) and a good solvent for said base material. As such a solvent, n-hexane, cyclohexane, n-pentane, cyclopentane, n-heptane, cycloheptane, toluene, freon, etc., can be used. The concentration of the base material is about 5-50% by weight. One hundred parts by weight of this solution of base material is mixed with 0.5-150 parts by weight of the solution of Nicorandil (salt) mentioned above and agitated, which allows fine crystals of Nicorandil (salt) to precipitate out of solution. The mean particle size of the precipitated Nicorandil (salt) depends on the concentration of the Nicorandil (salt), the kind of solvent, the temperature, and so on, but is usually 2-30 $\mu$m. When a tape is to be prepared, it is possible to apply this suspension of Nicorandil (salt) to the support mentioned above, to dry it, and to remove thereby almost all of the solvents (the good solvent and the poor solvent mentioned above). In this way, it is possible to obtain a tape in which there are fine crystals of Nicorandil (salt) in a layer of base material. If the suspension mentioned above is applied to an appropriate separation paper, and dried, after which the layer of base material formed can be pasted to the support mentioned above, a tape can also be obtained. An ointment can be obtained by the removal of the solvents so as to concentrate the suspension of Nicorandil (salt) mentioned above. The diameter of the particles of the Nicorandil (salt) obtained is 2 $\mu$m or more, is usually 2-50 $\mu$m, and preferably is 4-30 $\mu$m.

By the methods of manufacture mentioned above, the precipitated Nicorandil (salt) obtained during the manufacturing process ordinarily exists in the solvent, dispersed uniformly throughout the base material. For that reason, it is possible to obtain a pharmaceutical preparation with Nicorandil (salt) that is uniform in diameter and that moreover is uniformly distributed in the base material. With the use of this kind of pharmaceutical preparation, there are the advantages that said Nicorandil (salt) will remain stable, without being decomposed, and that the Nicorandil (salt) will be absorbed effectively through the skin at a fixed rate because the greater part of the Nicorandil (salt) is uniformly dispersed in the pharmaceutical preparation in the form of fine particles. By these methods, there is no need for a step in which the powdered Nicorandil (salt) is sieved.

Example 1.1

| | |
|---|---|
| Silicone rubber | 100 parts by weight |
| Nicorandil (Mean diameter: 12 $\mu$m) | 3 parts by weight |

To 200 parts by weight of a solution of 50% by weight of silicone rubber (trade name, Silascon 355 Medical Adhesive; Dow Corning Corp.) in freon, 3 parts by weight of Nicorandil suspended in cyclohexane was added. The mixture was agitated in a dissolver to give a suspension in which the Nicorandil was dispersed almost completely uniformly. The suspension was applied to a release liner of polyethyleneterephthalate so that its thickness would be 100 $\mu$m after being dried, which gave an adhesive layer. This adhesive layer was applied to a polyethylene film support, which resulted in a tape. This tape had an adhesive layer in which the Nicorandil was uniformly distributed, and in which the Nicorandil had the mean diameter of 12 $\mu$m. The amount of Nicorandil that was included was 0.29 mg/cm$^2$.

This tape was placed in aluminum packaging, into which a desiccant was placed, after which the package was sealed and stored at 50° C. for one week. The amount of Nicorandil in the tape was measured, and the percentage of Nicorandil remaining was calculated. Separately, a fresh preparation of tape measuring 3 cm $\times$ 3 cm was made to adhere on the back of a rat from which the hair had been removed with a shaver, and left for 48 hours; then the area under the blood concentration vs. time curve, or AUC$_{48}$ (ng.hr/ml) was found. The results are shown in Table 1. Example 1.1-1.8 and Comparative Examples 1.1-1.3 were all done with the same measurements being made, and those results are also shown in Table 1.

Example 1.2

| | |
|---|---|
| SIS | 25 parts by weight |
| Polyisoprene rubber | 25 parts by weight |
| Terpene resin | 50 parts by weight |
| Nicorandil | 3 parts by weight |
| (Mean diameter: 5.6 μm) | |

Instead of the silicone rubber, a base material composed of 25 parts by weight of SIS, 25 parts by weight of polyisoprene rubber, and 50 parts by weight of terpene resin was used. This base material was dissolved in cyclohexane at a concentration of 20% by weight. Except for the use of this solution instead of the freon solution, the procedures were carried out in the same way as in Example 1.1. The tape obtained had Nicroandil with a mean diameter of 5.6 μm dispersed uniformly throughout the adhesive layer, and the amount of Nicroandil was 0.29 mg/cm².

Example 1.3

| | |
|---|---|
| SIS | 25 parts by weight |
| Polyisoprene rubber | 25 parts by weight |
| Terpene resin | 50 parts by weight |
| Nicorandil | 3 parts by weight |
| (Mean diameter: 25 μm) | |

Except that the mean diameter of the Nicroandil was 25 μm, other conditions and procedures were the same as in Example 1.2. The tape obtained had Nicroandil with a mean diameter of 25 μm dispersed uniformly throughout the adhesive layer, and the amount of Nicroandil was 0.29 mg/cm².

Example 1.4

| | |
|---|---|
| SIS | 25 parts by weight |
| Polyisoprene rubber | 25 parts by weight |
| Terpene resin | 50 parts by weight |
| Nicorandil | 3 parts by weight |
| (Mean diameter: 35 μm) | |

Except that the mean diameter of the Nicorandil was 35 μm, other conditions and procedures were the same as in Example 1.2. The tape obtained had Nicorandil with a mean diameter of 35 μm dispersed uniformly throughout the adhesive layer, and the amount of Nicorandil was 0.29 mg/cm².

Example 1.5

| | |
|---|---|
| 1,4-cis-polybutadiene | 55 parts by weight |
| Natural rubber | 15 parts by weight |
| Terpene resin | 30 parts by weight |
| Nicorandil | 3 parts by weight |
| (Mean diameter: 12 μm) | |

Instead of the silicone rubber, a base material composed of 55 parts by weight of 1,4-cis-polybutadiene, 15 parts by weight of natural rubber, and 30 parts by weight of terpene resin was used. This base material was dissolved in cyclohexane at a concentration of 20% by weight. Except for the use of this solution instead of the freon solution, the procedures were carried out in the same way as in Example 1.1. The tape obtained had Nicorandil with a mean diameter of 12 μm dispersed uniformly throughout the adhesive layer, and the amount of Nicorandil was 0.29 mg/cm².

Example 1.6

| | |
|---|---|
| 1,4-cis-polybutadiene | 55 parts by weight |
| Natural rubber | 15 parts by weight |
| Terpene resin | 30 parts by weight |
| Nicorandil | 3 parts by weight |
| (Mean diameter: 4.3 μm) | |

Except that the mean diameter of the Nicorandil was 4.3 μm, other conditions and procedures were the same as in Example 1.5. The tape obtained had Nicorandil with a mean diameter of 4.3 μm dispersed uniformly throughout the adhesive layer, and the amount of Nicorandil was 0.29 mg/cm².

Example 1.7

| | |
|---|---|
| 1,4-cis-polybutadiene | 55 parts by weight |
| Natural rubber | 15 parts by weight |
| Terpene resin | 30 parts by weight |
| Nicorandil | 3 parts by weight |
| (Mean diameter: 27 μm) | |

Except that the mean diameter of the Nicorandil was 27 μm, other conditions and procedures were the same as in Example 1.5. The tape obtained had Nicorandil with a mean diameter of 27 μm dispersed uniformly throughout the adhesive layer, and the amount of Nicorandil was 0.29 mg/cm².

Comparative Example 1.1

| | |
|---|---|
| SIS | 25 parts by weight |
| Polyisoprene rubber | 25 parts by weight |
| Terpene resin | 50 parts by weight |
| Nicorandil | 3 parts by weight |
| (Mean diameter: 1.5 μm) | |

Except that the mean diameter of the Nicorandil was 1.5 μm, other conditions and procedures were the same as in Example 1.2. The tape obtained had Nicorandil with a mean diameter of 1.5 μm dispersed uniformly throughout the adhesive layer, and the amount of Nicorandil was 0.29 mg/cm².

Comparative Example 1.2

| | |
|---|---|
| Polybutyl acrylate | 100 parts by weight |
| Nicorandil | 3 parts by weight |
| (Mean diameter: 12 μm) | |

Procedures were the same as in Example 1.1 except that polybutyl acrylate was used instead of the silicone rubber, and that this was put into a 20% solution by weight of ethyl acetate. The tape obtained had Nicorandil dissolved throughout the adhesive layer, and the amount of Nicorandil was 0.29 mg/cm².

Example 1.8

| | |
|---|---|
| 1,4-cis-polybutadiene | 55 parts by weight |
| Natural rubber | 15 parts by weight |
| Terpene resin | 30 parts by weight |
| Nicorandilfumarate | 7.75 parts by weight |

-continued (Mean diameter: 13 μm)

Procedures were the same as in Example 1.5 except that 7.75 parts by weight of Nicorandilfumarate (mean diameter: 13 μm) was used instead of Nicorandil. The tape obtained had Nicorandilfumarate with a mean diameter of 13 μm dispersed uniformly throughout the adhesive layer, and the amount of Nicorandil was 0.464 mg/cm$^2$.

Comparative Example 1.3

| 1,4-cis-polybutadiene | 55 parts by weight |
|---|---|
| Natural rubber | 15 parts by weight |
| Terpene resin | 30 parts by weight |
| Nicorandilfumarate | 7.75 parts by weight |
| (Mean diameter: 1.5 μm) | |

Except that the mean diameter of the Nicroandilfumarate was 1.5 μm, other conditions and procedures were the same as in Example 1.8. The tape obtained had Nicroandilfumarate with a mean diameter of 1.5 μm dispersed uniformly throughout the adhesive layer, and the amount of Nicorandil was 0.464 mg/cm$^2$.

TABLE 1

| | Remaining Nicorandil (salt) (%) (50° C. × 1 week) | AUC$_{48}$ (ng.hr/ml) |
|---|---|---|
| Example 1.1 | 85.3 | 795 |
| Example 1.2 | 66.2 | 891 |
| Example 1.3 | 86.2 | 632 |
| Example 1.4 | 90.5 | 387 |
| Example 1.5 | 87.1 | 867 |
| Example 1.6 | 83.2 | 926 |
| Example 1.7 | 60.1 | 922 |
| Comparative Example 1.1 | 1.2 | 924 |
| Comparative Example 1.2 | 0.8 | 851 |
| Example 1.8 | 99.7 | 1022 |
| Comparative Example 1.3 | 7.1 | 1124 |

Example 1.9

| Silicone rubber | 100 parts by weight |
|---|---|
| Nicorandil | 3 parts by weight |
| Salicylic acid | 3 parts by weight |

To 200 parts by weight of a solution of 50% by weight of silicone rubber (trade name, Silascon 355, Medical Adhesive; Dow Corning Corp.) in freon, three parts by weight of Nicorandil dissolved in 75 parts by weight of tetrahydrofuran and also 3 parts by weight of salicylic acid dispersed in cyclohexane were added. The mixture was agitated in a dissolver to give a suspension in which the drugs (Nicorandil, Nicorandilsalicylate, and salicylic acid) were dispersed almost completely uniformly. This was applied to a release liner of polyethyleneterephthalate so that its thickness would be 100 μm after being dried, which gave an adhesive layer. This adhesive layer was applied to a polyethylene film support, which resulted in a tape. This tape had an adhesive layer in which the drugs were uniformly distributed and in which the drugs had a mean diameter of 13 μm. The amount of Nicorandil that was included was 0.283 mg/cm$^2$. This tape was used to make measurements the same as those in Example 1.1. However, the storage period for the tape was 3 weeks. These results are shown in Table 2. Examples 1.10 to 1.14 and Comparative Examples 1.4 and 1.5 were conducted with the same measurements being made, and those results are also shown in Table 2.

Example 1.10

| SIS | 25 parts by weight |
|---|---|
| Polyisoprene rubber | 25 parts by weight |
| Terpene resin | 50 parts by weight |
| Nicorandil | 3 parts by weight |
| Oxalic acid | 3 parts by weight |

A base material is composed of 25 parts by weight of SIS, 25 parts by weight of polyisoprene rubber, and 50 parts by weight of terpene resin. In a solution of 20 percent by weight of the base material in cyclohexane, Nicorandil dissolved in 75 parts by weight of tetrahydrofuran (THF), and oxalic acid suspended in cyclohexane were added, and the mixture was agitated in a dissolver. A suspension in which the particles of the drugs (Nicorandil, Nicorandiloxalate, and oxalic acid) were almost completely uniformly dispersed was obtained. With the use of this suspension, a tape was made following the procedures of Example 1.9. This tape had an adhesive layer in which the drugs were uniformly distributed and in which the drugs had a mean diameter of 4.1 μm. The amount of Nicorandil that was included was 0.283 mg/cm$^2$.

Example 1.11

| SIS | 25 parts by weight |
|---|---|
| Polyisoprene rubber | 25 parts by weight |
| Terpene resin | 50 parts by weight |
| Nicorandil | 3 parts by weight |
| (Mean diameter: 38 μm) | |
| Oxalic acid | 3 parts by weight |

Except for the use of a suspension of Nicorandil in cyclohexane instead of the solution of Nicorandil in THF, and for the use of a solution of oxalic acid in THF (75 parts by weight) instead of the suspension of oxalic acid in cyclohexane, the procedures were the same as in Example 1.9. The tape that was obtained had drugs dispersed therein (Nicorandil, Nicorandiloxalate and oxalic acid) the mean particle size of which was 36 μm, which particles were uniformly dispersed, and the amount of Nicorandil in the tape was 0.283 mg/cm$^2$.

Example 1.12

| SIS | 25 parts by weight |
|---|---|
| Polyisoprene rubber | 25 parts by weight |
| Terpene resin | 50 parts by weight |
| Nicorandil | 3 parts by weight |
| (Mean diameter: 24 μm) | |
| Oxalic acid | 3 parts by weight |

Except that the mean diameter of the Nicorandil was 24 μm, other conditions and procedures were the same as in Example 1.11. The tape obtained had the drugs (Nicorandil, Nicorandil oxalate and oxalic acid) with a mean diameter of 22 μm dispersed uniformly throughout the adhesive layer, and the amount of Nicorandil was 0.283 mg/cm$^2$.

Example 1.13

| | |
|---|---|
| 1,4-cis-polybutadiene | 55 parts by weight |
| Natural rubber | 15 parts by weight |
| Terpene resin | 30 parts by weight |
| Nicorandil | 3 parts by weight |
| Fumaric acid | 3 parts by weight |

A base material was utilized that was composed of 55 parts by weight of 1,4-cis-polybutadiene, 15 parts by weight of natural rubber, and 30 parts of terpene resin. In a solution of 20% by weight of the base material in cyclohexane, a solution of Nicorandil in THF (75 parts by weight) and a suspension of fumaric acid in cyclohexane were added, and the mixture was agitated in a dissolver. A suspension was obtained in which the particles of the drugs (Nicorandil, Nicorandilfumarate and fumaric acid) were almost completely uniformly dispersed. With the use of this suspension, a tape was made following the procedures of Example 1.9. This tape had an adhesive layer in which the drugs were uniformly distributed and in which the drugs had a mean diameter of 12 µm. The amount of Nicorandil that was included in the tape was 0.283 mg/cm$^2$.

Example 1.14

| | |
|---|---|
| 1,4-cis-polybutadiene | 55 parts by weight |
| Natural rubber | 15 parts by weight |
| Terpene resin | 30 parts by weight |
| Nicorandil | 3 parts by weight |
| Fumaric acid | 3 parts by weight |

Except for the use of a mixture of cyclohexane:THF (1:1) in which the base material was dissolved, the procedures were the same as those of Example 1.13. A tape was obtained in which the drug particles with a mean diameter of 4.2 µm were evenly dispersed throughout the adhesive layer and in which the amount of Nicorandil was 0.283 mg/cm$^2$.

Comparative Example 1.4

| | |
|---|---|
| Polybutyl acrylate | 100 parts by weight |
| Nicorandil | 3 parts by weight |
| Salicylic acid | 3 parts by weight |

Except for the use of a 20% (by weight) solution of polybutyl acrylate in ethyl acetate instead of the solution of silicone rubber in freon, the procedures were the same as those of Example 1.9. A tape was obtained in which the drug was dissolved throughout the adhesive layer, and in which the amount of Nicroandil was 0.283 mg/cm$^2$.

Comparative Example 1.5

| | |
|---|---|
| 1,4-cis-polybutadiene | 55 parts by weight |
| Natural rubber | 15 parts by weight |
| Terpene resin | 30 parts by weight |
| Nicorandil | 3 parts by weight |
| Fumaric acid | 3 parts by weight |

Except for the use of THF in which the base material was dissolved, the procedures were the same as those of Example 1.13. A tape was obtained in which drug particles with a mean diameter of 1.7 µm were evenly dispersed throughout the adhesive layer, and in which the amount of Nicorandil was 0.283 mg/cm$^2$.

TABLE 2

| | Remaining amount (%) (50° C. × 1 week) | AUC$_{48}$ (ng.hr/ml) |
|---|---|---|
| Example 1.9 | 99.4 | 731 |
| Example 1.10 | 91.5 | 851 |
| Example 1.11 | 99.3 | 381 |
| Example 1.12 | 99.1 | 607 |
| Example 1.13 | 99.7 | 893 |
| Example 1.14 | 96.8 | 1002 |
| Comparative Example 1.4 | 2.1 | 893 |
| Comparative Example 1.5 | 3.2 | 1080 |

Example 2.1 (Ointment)

| | |
|---|---|
| Nicorandil | 2 parts by weight |
| 1-dodecylazacycloheptane-2-one (AZONE) | 5 parts by weight |
| Plastibase | 93 parts by weight |

Two parts of Nicorandil by weight and 5 parts of AZONE by weight were put together in a mixing and grinding machine and mixed together in vacuo with the gradual addition of plastibase until a homogeneous ointment was obtained. The mean diameter of the Nicorandil in the ointment was 25 µm.

The ointment obtained was put into an airtight plastic container and stored at 50° C. for 2 weeks. After storage, the amount of Nicorandil in the ointment was assayed, and the amount remaining was calculated. Separately, 0.5 g of freshly prepared ointment was applied uniformly to a 4×4 cm$^2$ area of the back of a rat that had had its hair removed with a shaver, and 48 hours later, the area under the blood concentration vs. time curve, or AUC$_{48}$, expressed as ng.hr/ml, was calculated. The calculation of AUC$_{48}$×(% remaining/100) was made, and this was called the "stability parameter". These results are shown in Table 3. The same kinds of measurements were made in Examples 2.2 and 2.3, and Comparative Examples 2.1 to 2.3, and those results also are shown in Table 3.

Comparative Example 2.1

Except for the use of the same amounts of poly(oxyethylene) (9) laurylether instead of AZONE, the procedures were the same as in Example 2.1.

Example 2.2 (Ointment)

| | |
|---|---|
| Nicorandilfumarate | 3.1 parts by weight |
| AZONE | 8 parts by weight |
| Plastibase | 88.9 parts by weight |

Eight parts by weight of AZONE and 3.1 parts by weight of Nicorandilfumarate were put into a mixing and grinding machine, and mixed together in vacuo with the gradual addition of plastibase, which resulted in a homogeneous ointment. The mean diameter of the Nicorandil in the ointment was 30 µm.

Comparative Example 2.2

Except for the use of poly(oxyethylene) (6) sorbitan monooleate instead of the AZONE, the procedures were the same as in Example 2.2.

Example 2.3 (Ointment)

| | |
|---|---|
| Nicorandil | 2 parts by weight |
| AZONE | 5 parts by weight |
| Fumaric acid | 2 parts by weight |
| Plastibase | 91 parts by weight |

Two parts by weight of Nicorandil, 5 parts by weight of AZONE, and 2 parts by weight of fumaric acid were put into a mixing and grinding machine, and mixed together in vacuo with the gradual addition of plastibase, which resulted in a homogeneous ointment. The mean diameter of the drugs (Nicorandil, Nicorandilfumarate and fumaric acid) in the ointment was 15 μm.

Comparative Example 2.3

Except for the use of lauroyldiethanolamide instead of the AZONE, the procedures were the same as in Example 2.3.

TABLE 3

| | Remaining amount (%) (50° C. × 2 weeks) | $AUC_{48}$ (ng · hr/ml) | Stability parameter |
|---|---|---|---|
| Example 2.1 | 63.0 | 23400 | 14742 |
| Comparative Example 2.1 | 13.3 | 17200 | 2288 |
| Example 2.2 | 92.2 | 26842 | 24748 |
| Comparative Example 2.2 | 26.3 | 13310 | 3500 |
| Example 2.3 | 90.6 | 24760 | 22433 |
| Comparative Example 2.3 | 3.9 | 27918 | 1089 |

Example 2.4

| | |
|---|---|
| Polyvinylisobutylether | 70 parts by weight |
| Polyvinylethylether | 30 parts by weight |
| Nicorandil (Mean diameter: 13 μm) | 5 parts by weight |
| AZONE | 5.53 parts by weight |

To a cyclohexane solution containing a mixture of 70 parts by weight of polyvinylisobutylether (trade name, Lutonal IC 125; BASF Co.) and 30 parts y weight of polyvinylethylether (trade name, Lutonal A50; BASF Co.) in a concentration of 15%, a suspension of 5 parts by weight of Nicorandil in cyclohexane and 5.53 parts by weight of AZONE were added. This mixture was agitated in a dissolver, and a suspension in which the Nicorandil was almost completely uniformly dispersed was obtained. This was applied to a release paper liner of polyethyleneterephthalate so that its thickness would be 100 μm after being dried. The surface of the adhesive layer that was formed was applied to a polyethylene support, to give a tape. The mean diameter of the Nicorandil was 13 μm, and the Nicorandil was uniformly dispersed in the adhesive layer of the tape that was obtained; the amount of the Nicorandil was 0.45 mg/cm² of tape.

The same test procedure as in Example 1.1 was repeated using this tape. The results are shown in Table 4. Example 2.5 and Comparative Examples 2.4 and 2.5 were conducted using the same procedure. Those results are also shown in Table 4.

Comparative Example 2.4

Except for the use of oleoylsarcosine instead of AZONE in the same amounts, the procedures were the same as in Example 2.4

Example 2.5

| | |
|---|---|
| Polyvinylisobutylether | 70 parts by weight |
| Polyvinylethylether | 30 parts by weight |
| Nicorandilfumarate | 7.75 parts by weight |
| AZONE | 5.53 parts by weight |

Except for the use of 7.75 parts by weight of Nicorandilfumarate (mean diameter: 12 μm) instead of 5 parts by weight of Nicorandil, the procedures were the same as in Example 2.4. A tape containing 0.44 mg of Nicorandil per cm² was obtained.

Comparative Example 2.5

Except for the use of lauroyldiethanolamide instead of AZONE in the same amounts, the procedures were the same as in Example 2.5

TABLE 4

| | Remaining amount (%) (50° C. × 1 week) | $AUC_{48}$ (ng · hr/ml) | Stability parameter |
|---|---|---|---|
| Example 2.4 | 58.3 | 8870 | 5171 |
| Comparative Example 2.4 | 1.2 | 9182 | 110 |
| Example 2.5 | 90.7 | 7920 | 7183 |
| Comparative Example 2.5 | 4.0 | 8497 | 340 |

It can be seen from Tables 3 and 4 that the values of the stability parameters of the pharmaceutical preparation of this invention, namely, the product of 1/100 of the residual ratio (the index of drug stability) and $AUC_{48}$ (the index of drug absorption), are large. These results show that the absorbability of the drugs (Nicorandil (salt)) of the formulation of this invention is good, and that the stability of said drugs is excellent.

Example 3.1

| | |
|---|---|
| 1,4-cis-polybutadiene | 80 parts by weight |
| Natural rubber | 20 parts by weight |
| Terpene resin | 20 parts by weight |
| Nicorandil | 10 parts by weight |
| Fumaric acid | 10 parts by weight |
| Isopropyl myristate | 53.7 parts by weight |
| N-lauroylsarcosine | 5.37 parts by weight |

A base material is composed of 80 parts by weight of 1,4-cis-polybutadiene, 20 parts by weight of natural rubber and 20 parts by weight of terpene resin. This base material was dissolved in cyclohexane at a concentration of 15% (by weight). To 100 parts by weight of polymer ingredients in the solution, a THF solution containing 10 parts by weight of Nicorandil, 10 parts by weight of fumaric acid, 5.37 parts by weight of N-lauroylsarcosine (an absorbefacient), and 53.7 parts by weight of isopropyl myristate (an absorbefacient and stabilizer) was added. This mixture was agitated in a dissolver, and a suspension that contained the drugs (Nicorandil, Nicorandilfumarate and fumaric acid) in a uniform suspension was obtained. This suspension was applied to a release liner of polyethyleneterephthalate so that its thickness would be 100 μm after being dried. The surface of the adhesive layer that was formed was applied to a polyethylene film support, to give a pharmaceutical preparation in the form of tape. This pharmaceutical tape had an adhesive layer in which the mean diameter of the drugs contained in it was 7 μm, and the amount of Nicorandil was 0.56 mg/cm$^2$ of tape.

The same test procedure as in Example 1.1 for the amount of drug remaining and the AUC$_{48}$ was repeated using the tape, and the stability parameter was calculated. The results are shown in Table 5. In Comparative Examples 3.1 and 3.2, the same measurements were also made. These results are also shown in Table 5.

Comparative Example 3.1

The procedures were the same as in Example 3.1, except that N-lauroylsarcosine (an absorbefacient) was not added.

Comparative Example 3.2

The procedures were the same as in Example 3.1, except that isopropyl myristate and N-lauroylsarcosine were not added.

TABLE 5

|  | Absorbefacient | AUC$_{48}$ | Remaining amount (%) | Stability parameter |
|---|---|---|---|---|
| Example 3.1 | Isopropyl myristate + N-lauroyl-sarcosine | 9125 | 95.2 | 8687 |
| Comparative Example 3.1 | Isopropyl myristate | 1850 | 99.2 | 1835 |
| Comparative Example 3.2 | — | 1205 | 97.2 | 1171 |

Example 3.2 (Ointment)

| Nicorandil | 5 parts by weight |
|---|---|
| Isopropyl palmitate | 25 parts by weight |
| Lauloyldiethanolamide | 2.5 parts by weight |
| Plastibase | 67.5 parts by weight |

Five parts by weight of Nicorandil, 25 parts by weight of isopropyl palmitate, and 2.5 parts by weight of lauroyldiethanolamide were placed in a mixing and grinding machine and mixed together in vacuo with the gradual addition of 67.5 parts by weight of plastibase to give an ointment. The mean diameter of the Nicorandil in the ointment was 17 μm, and the particles of Nicorandil were dispersed uniformly.

The same test procedure as in Example 2.1 for the amount of drug remaining and the AU$_{48}$ was repeated using the ointment, and the stability parameter was calculated. The storage time for the ointment was 1 week. The results are shown in Table 6. Measurements were made in the same way as in Comparative Examples 3.3 to 3.5. Those results are also shown in Table 6.

Comparative Example 3.3 (Ointment)

The procedures were the same as in Example 3.2, except that isopropyl palmitate (an absorbefacient and stabilizer) was not added.

Comparative Example 3.4

The procedures were the same as in Example 3.2, except that lauroyldiethanolamide (an absorbefacient) was not added.

Comparative Example 3.5

The procedures were the same as in Example 3.2, except that isopropyl palmitate and lauroyldiethanolamide were not added.

TABLE 6

|  | Absorbefacient | AUC$_{48}$ | Remaining amount (%) | Stability parameter |
|---|---|---|---|---|
| Example 3.2 | Isopropyl palmitate + lauroyldi-ethanolamide | 22180 | 79.0 | 17522 |
| Comparative Example 3.3 | lauroyldi-ethanolamide | 20300 | 8.2 | 1665 |
| Comparative Example 3.4 | Isopropyl palmitate | 2300 | 87.2 | 2006 |
| Comparative Example 3.5 | — | 2020 | 85.2 | 1721 |

Example 3.3

| Polyvinylisobutylether | 70 parts by weight |
|---|---|
| Polyvinylethylether | 30 parts by weight |
| Nicorandiloxalate | 15 parts by weight |
| Isopropyl myristate | 30 parts by weight |
| Lauroyldiethanolamide | 3 parts by weight |

A cyclohexane solution containing a mixture of 70 parts by weight of polyvinylisobutylether (trade name Lutonal IC 125; BASF Co.) and 30 parts by weight of polyvinylethylether (trade name, Lutonal A50; BASF Co.) at a concentration of 15% by weight was prepared. For each 100 parts by weight of polymer ingredients in the solution, a solution of THF containing 15 parts by weight of Nicorandiloxalate, 3 parts by weight of lauroyldiethanolamide (an absorbefacient) and 30 parts by weight of isopropyl myristate (an absorbefacient and stabilizer) was added. This mixture was agitated in a dissolver, and a suspension in which the drugs were uniformly dispersed was obtained. This suspension was applied to a release liner of polyethyleneterephthalate so that its thickness would be 100 μm after being dried. The surface of the adhesive layer that was formed was applied to a polyethylene film support, so as to give a pharmaceutical preparation in the form of tape. This pharmaceutical tape had an adhesive layer in which the mean diameter of the Nicorandiloxalate was 11 μm and in which the Nicorandiloxalate was uniformly dispersed. The same test procedure as in Example 1.1 for the amount of drug remaining and the AUC$_{48}$ was repeated using the tape, and the stability parameter was calculated. The results are shown in Table 7. In Comparative Examples 3.6 to 3.8, the same measurements were also made. These results are also shown in Table 7.

Comparative Example 3.6

The procedures were the same as in Example 3.3, except that isopropyl myristate (an absorbefacient and stabilizer) was not added.

Comparative Example 3.7

The procedures were the same as in Example 3.3, except that lauroyldiethanolamide (an absorbefacient) was not added.

Comparative Example 3.8

The procedures were the same as in Example 3.3, except that isopropyl myristate and lauroyldiethanolamide were not added.

TABLE 7

|  | Absorbefacient | AUC$_{48}$ | Remaining amount (%) | Stability parameter |
|---|---|---|---|---|
| Example 3.3 | Isopropyl myristate + lauroyldi- ethanolamide | 9540 | 92.1 | 8786 |
| Comparative Example 3.6 | Lauroyldi- ethanolamide | 8870 | 18.3 | 1623 |
| Comparative Example 3.7 | Isopropyl myristate | 1750 | 99.4 | 1739 |
| Comparative Example 3.8 | — | 1150 | 96.8 | 1113 |

Example 4

| 1,4-cis-polybutadiene | 55 parts by weight |
|---|---|
| Natural rubber | 15 parts by weight |
| Terpene resin | 30 parts by weight |
| Nicorandil | 3 parts by weight |

A base material was composed of 55 parts by weight of 1,4-cis-polybutadiene, 15 parts by weight by weight of natural rubber, and 30 parts by terpene resin. This base material was dissolved in cyclohexane at the concentration of 20% by weight. To this solution, a 75 parts (by weight) THF solution containing Nicorandil at a concentration of 3 parts by weight was added, and the resulting mixture was agitated in a dissolver so that particles of Nicorandil precipitated out. In this way, a suspension was obtained in which fine crystals of Nicorandil were almost uniformly dispersed. This suspension was applied to a release liner of polyethyleneterephthalate so that its thickness would be 100 μm after being dried, and the whole was dried, so as to form an adhesive layer. The surface of the adhesive layer was applied to a polyethylene film support, so as to give a pharmaceutical preparation in the form of a tape. This pharmaceutical preparation in the form of a tape had an adhesive layer in which the mean diameter of the Nicorandil was 14 μm and in which the Nicorandil was uniformly dispersed; the amount of Nicorandil was 0.29 mg/cm$^2$ of tape.

The same test procedure as in Example 1.1 for the amount of drug remaining and the AUC$_{48}$ was repeated using the tape, and the stability parameter was calculated. The amount of drug remaining was 90.2%, and the AUC$_{48}$ was about 873 ng.hr/ml.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A pharmaceutical preparation for percutaneous absorption comprising a base material which is not compatible with Nicorandil and Nicorandil which may be in a free form or in the form of a salt thereof and is evenly distributed throughout said base material, wherein said Nicorandil exists as fine crystals having a mean diameter of between 2 and 50 μm whereby the stability of Nicorandil in said preparation during storage is greatly improved.

2. A pharmaceutical preparation according to claim 1, wherein said base material is hydrophobic.

3. A pharmaceutical preparation according to claim 2, wherein said base material is an adhesive rubber base material.

4. A pharmaceutical preparation according to claim 3, wherein said adhesive rubber base material is 1,4-cis-polybutadiene.

5. A pharmaceutical preparation according to claim 4, wherein said 1,4-cis-polybutadiene is used in a proportion of 20-80% by weight in the base material.

6. A pharmaceutical preparation according to claim 3, wherein said adhesive rubber base material is an adhesive of silicone rubber.

7. A pharmaceutical preparation according to claim 1, wherein said mean diameter of granules of Nicorandil and/or its salts is 4-30 μm.

8. A pharmaceutical preparation according to claim 1, wherein said Nicorandil salts are organic salts of Nicorandil, organic acids constituting said salts being at least one selected from the group consisting of fumaric acid, oxalic acid, salicylic acid, tartaric acid, glutaric acid, maleic acid, and p-toluenesulfonic acid.

9. A pharmaceutical preparation according to claim 1, wherein said preparation has at least one organic acid selected from the group consisting of fumaric acid, oxalic acid, salicylic acid, tartaric acid, glutaric acid, maleic acid, and p-toluenesulfonic acid.

10. A pharmaceutical preparation according to claim 1, wherein said absorbefacient for percutaneous absorption is 1-dodecylazacycloheptane-2-one.

11. A pharmaceutical preparation according to claim 1, wherein said absorbefacient for percutaneous absorption is a combination of fatty esters and compounds that have an amide bond, said compounds that have an amide bond being at least one selected from the group consisting of N-acylsarcosine monoethanolamides derived from fatty acids, diethanolamides derived from fatty acids, alkyleneoxide adducts of monoethanolamides derived from fatty acids, and alkyleneoxide adducts of diethanolamides derived from fatty acids.

12. A pharmaceutical preparation according to claim 11, wherein said fatty esters are formed by fatty acids with a carbon number of from 10 to 18 and alcohols with a carbon number of from 1 to 20.

13. A pharmaceutical preparation according to claim 12, wherein said fatty esters are isopropyl myristate and/or isopropyl palmitate.

14. A pharmaceutical preparation according to claim 11, wherein the carbon number of acyl group of said N-acylsarcosine is from 6-18.

15. A pharmaceutical preparation according to claim 14, wherein said N-acylsarcosine is N-lauroylsarcosine.

16. A pharmaceutical preparation according to claim 11, wherein said monoethanolamides derived from fatty acids are lauroyl monoethanolamide and/or monoethanolamides of fatty acids derived from coconut oil, and the alkyleneoxide adducts of the monoethanolamides derived from fatty acids are polyoxyethylene adducts of the monoethanolamides of the fatty acid, derived from coconut oil.

17. A pharmaceutical preparation according to claim 11, wherein said diethanolamides derived from fatty acid are lauroyldiethanolamide and/or diethanolamides of the fatty acids derived from coconut oil.

18. A pharmaceutical preparation according to claim 1, wherein said absorbefacient for percutaneous absorption is present in a proportion of 1-100 parts by weight to 100 parts by weight of the base material.

19. A pharmaceutical preparation according to claim 1, wherein said fatty esters are present in a proportion of 1-80 parts by weight to 100 parts by weight of the base material, and the compounds that have an amide bond are present in a proportion of 0.01-30 parts by weight to 100 parts by weight of the base material.

20. A pharmaceutical preparation according to claim 1, wherein said preparation is a tape or an ointment.

21. A method for the manufacture of a pharmaceutical preparation for the percutaneous absorption comprising a base material which is not compatible with Nicorandil and Nicorandil which may be in a free form or in the form of a salt thereof and is evenly distributed throughout said base material, wherein said Nicorandil exists as fine crystals having a mean diameter of between 2 and 50 μm including:
dissolving the Nicorandil and/or its salts in a solvent that is a good solvent for said Nicorandil; and
dissolving the base material in a solvent that is a poor solvent for said Nicorandil;
mixing these two solutions to give a solution of a mixture that contains precipitated crystals of Nicorandil and/or its salts with a mean diameter of 2-50 μm; and
substantially removing said good solvent and said poor solvent from said solution of the mixture.

22. A method according to claim 21, wherein said solution of the mixture has absorbefacients for percutaneous absorption.

23. A method according to claim 21, wherein said base material is hydrophobic.

24. A method according to claim 23, wherein said base material is an adhesive rubber base material.

25. A method according to claim 24, wherein said adhesive rubber base material is 1,4-cis-polybutadiene.

26. A method according to claim 25, wherein said 1,4-cis-polybutadiene is used in a proportion of 20-80% by weight in said adhesive rubber base material.

27. A method according to claim 24, wherein said adhesive rubber base material is an adhesive of silicone rubber.

28. A method according to claim 21, wherein said good solvent is at least one selected from the solvents consisting of tetrahydrofuran, dichloromethane and chloroform, and the poor solvent is at least one selected from the solvents consisting of n-hexane, cyclohexane, n-pentane, cyclopentane, n-heptane, cycloheptane, toluene and freon.

29. A method according to claim 21, wherein said salts of Nicorandil are organic salts of Nicorandil, organic acids constituting said salts being at least one selected from the group consisting of fumaric acid, oxalic acid, salicylic acid, tartaric acid, glutaric acid, maleic acid, and p-toluenesulfonic acid.

30. A method according to claim 21, wherein said solution of the mixture has at least one selected from the group consisting of fumaric acid, oxalic acid, salicylic acid, tartaric acid, glutaric acid, maleic acid and p-toluenesulfonic acid.

31. A method according to claim 22, wherein said absorbefacient for percutaneous absorption is 1-dodecylazacycloheptane-2-one.

32. A method according to claim 22, wherein said absorbefacient for percutaneous absorption is a combination of fatty esters and compounds that have an amide bond, said compounds that have an amide bond are at least one compound selected from the group consisting of N-acylsarcosine, monoethanolamides derived from fatty acids, diethanolamides derived from fatty acids, alkyleneoxide adducts of monoethanolamides derived from fatty acids, and alkyleneoxide adducts of diethanolamides derived from fatty acids.

33. A method according to claim 32, wherein said fatty acid esters are esters formed from fatty acids with 10-18 carbons and alcohols with 1-20 carbons.

34. A method according to claim 33, wherein said fatty esters are isopropyl myristate and/or isopropyl palmitate.

35. A method according to claim 32, wherein the carbon number of acyl group of said N-acylsarcosine is from 6-18.

36. A method according to claim 35, wherein said N-acylsarcosine is N-lauroysarcosine.

37. A method according to claim 32, wherein said monoethanolamides derived from fatty acids are lauroyl monoethanolamide and/or monoethanolamides of fatty acids derived from coconut oil, and said alkyleneoxide adducts of the monoethanolamides derived from fatty acids are the polyoxyethylene adducts of the monoethanolamides of the fatty acid derived from coconut oil.

38. A method according to claim 32, wherein said diethanolamides derived from fatty acids are lauroyldiethanolamide and/or diethanolamides of fatty acids derived from coconut oil.

39. A method according to claim 22, wherein said absorbefacient for percutaneous absorption is present in a proportion of 1-100 parts by weight to 100 parts by weight of the base material.

40. A method according to claim 32, wherein said fatty esters are present in a proportion of 1-80 parts by weight to 100 parts by weight of the base material, said compounds that contain an amide bond being present in a proportion of 0.01-30 parts by weight to 100 parts by weight of the base material.

41. A method according to claim 21, comprising application of the solution mixture to a support, and substantial removal of the solvents by drying, resulting in a tape with an adhesive layer that contains said Nicorandil and/or its salts on the flexible supporting means.

42. A pharmaceutical preparation according to claim 1 wherein said preparation further comprises an absorbefacient for percutaneous absorption which does not adversely affect the stability of Nicorandil.

* * * * *